US012045938B2

(12) United States Patent
Adawi et al.

(10) Patent No.: US 12,045,938 B2
(45) Date of Patent: Jul. 23, 2024

(54) ANATOMICAL MODELING WITH THE BALL-PIVOTING ALGORITHM

(71) Applicant: BIOSENSE WEBSTER (ISRAEL) LTD., Yokneam (IL)

(72) Inventors: Eid Adawi, Tur'an (IL); Fady Massarwa, Baka Al Gharbiyya (IL); Roy Urman, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 109 days.

(21) Appl. No.: 17/889,319

(22) Filed: Aug. 16, 2022

(65) Prior Publication Data

US 2024/0062464 A1  Feb. 22, 2024

(51) Int. Cl.
*G06T 17/20* (2006.01)
(52) U.S. Cl.
CPC .......... *G06T 17/20* (2013.01); *G06T 2210/41* (2013.01)
(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker |
| 6,177,792 B1 | 1/2001 | Govari |
| 6,690,963 B2 | 2/2004 | Ben-Haim |
| 6,788,967 B2 | 9/2004 | Ben-Haim |
| 8,456,182 B2 | 6/2013 | Bar-Tal |
| 9,265,434 B2 | 2/2016 | Merschon |
| 9,947,142 B2 * | 4/2018 | Voth ........................ G06T 19/20 |
| 9,980,653 B2 * | 5/2018 | Lichtenstein ............ A61B 5/06 |
| 2009/0244061 A1 | 10/2009 | De Putter |
| 2018/0158252 A1 | 6/2018 | Stehle |
| 2019/0183367 A1 * | 6/2019 | Turgeman ................ A61B 8/12 |
| 2020/0211280 A1 * | 7/2020 | Cohen ..................... G06T 15/06 |
| 2020/0349762 A1 | 11/2020 | Nolan |

(Continued)

FOREIGN PATENT DOCUMENTS

WO    WO2021123403 A1    6/2021

OTHER PUBLICATIONS

Bernardini, Fausto, et al., "The ball-pivoting algorithm for surface reconstruction," IEEE transactions on visualization and computer graphics 5.4 (1999): 349-359.

(Continued)

*Primary Examiner* — Nurun Flora

(57) ABSTRACT

A system includes a display and a processor. The processor is configured to obtain a point cloud including multiple points representing different respective locations in a body of a subject, the points being labeled as corresponding to respective anatomical structures to which the locations, respectively, belong. The anatomical structures including a first structure and multiple second structures. The processor is further configured to compute a mesh including multiple triangles representing the anatomical structures, by applying a ball-pivoting algorithm to the point cloud with a constraint that none of the triangles include two of the points labeled as corresponding to different respective ones of the second structures. Other examples are also described.

20 Claims, 3 Drawing Sheets

(56) References Cited

U.S. PATENT DOCUMENTS

2021/0166397 A1   6/2021  Albrecht
2021/0295549 A1*  9/2021  Govari ................... G06T 17/10

OTHER PUBLICATIONS

Lorensen, William E. and Harvey E. Cline, "Marching cubes: A high resolution 3D surface construction algorithm," ACM siggraph computer graphics 21.4 (1987): 163-169.

* cited by examiner

ANATOMICAL MODELING WITH THE BALL-PIVOTING ALGORITHM

FIELD OF THE DISCLOSURE

The present disclosure is related to the field of anatomical modeling.

BACKGROUND

A three-dimensional anatomical model often includes a mesh interpolating a point cloud. Such a mesh may be constructed using the ball-pivoting algorithm (BPA), which is described, for example, in Bernardini, Fausto, et al., "The ball-pivoting algorithm for surface reconstruction," IEEE transactions on visualization and computer graphics 5.4 (1999): 349-359, whose disclosure is incorporated herein by reference. Per the BPA, three points form a triangle if a ball of a user-specified radius touches them without containing any other point. Starting with a seed triangle, the ball pivots around an edge (i.e., it revolves around the edge while keeping in contact with the edge's endpoints) until it touches another point, forming another triangle (or other polygon from which the mesh is formed). The process continues until all reachable edges have been tried, and then starts from another seed triangle, until all points have been considered. The process can then be repeated with a ball of larger radius to handle uneven sampling densities.

Anatomical models, and electro-anatomical models in particular, are commonly used by electrophysiologists to visualize the anatomy and electrical signals in cardiac tissues. These models may be built algorithmically using data gathered by diagnostic catheters and/or ultrasound data, and such models often comprise 3D triangulated meshes corresponding to individual anatomical structures of the heart. Triangular meshes are typical, but not required, as meshes may also comprises quadrangles in some systems within the scope of some examples. A 3D model including more than one structure of the heart may be formed by piecing together the individual 3D meshes generated. Example anatomical structures that may be modeled include, for example, left atrial (LA) body and left atrial appendage (LAA), left inferior pulmonary vein (LIPV), left superior pulmonary (LSPV), right inferior pulmonary vein (RIPV), and right superior pulmonary vein (RSPV). As an example, a 3D mesh representing a left atrium may be connected to other 3D meshes representing pulmonary veins, arteries and/or other chambers. Image processing is typically required to connect the individual 3D meshes such that the full model may be displayed to the user. Color coding may be superimposed on the model to show propagation of an electrical signal across the chamber or to show other EP properties of the heart. The user expects to see signal propagation in the atrium and ventricle but not in the pulmonary veins and arteries. The border line (or anatomical structures boundary) between the atrium/ventricle and the veins/arteries currently generally must be defined manually by the user so that signal propagation mapping does not cross into the veins and arteries.

BRIEF DESCRIPTION OF THE DRAWINGS

The present disclosure will be more fully understood from the following detailed description of examples thereof, taken together with the drawings, in which.

DETAILED DESCRIPTION OF EXAMPLES

Overview

In many cases, using the BPA to build an anatomical model may be challenging. First, the model may erroneously join together two anatomical structures—such as two pulmonary veins—that are not actually joined to one another, but are separated from one another by a distance that is less than the diameter of the BPA ball. Second, the model may fail to accurately mark the boundary between two joined anatomical structures, such as a left atrium body and a pulmonary vein.

Examples of the present disclosure therefore modify the BPA so as to address these challenges. The modified algorithm is applied to a point cloud in which each point is labeled with an identifier of the anatomical structure to which the point belongs.

In particular, as a triangle mesh is built from the labeled points, preferably no pair of points from different respective unjoined structures are allowed to belong to the same triangle. This constraint may reduce the spurious joining of anatomical structures is avoided. In addition, any triangle edge that joins a pair of points from different respective structures may be marked. Following the building of the mesh, the marked edges, which define one or more closed polylines, may then be smoothed. The resulting closed curves are then overlayed on the model to indicate the boundaries between the joined anatomical structures.

System Description

Figure 1:
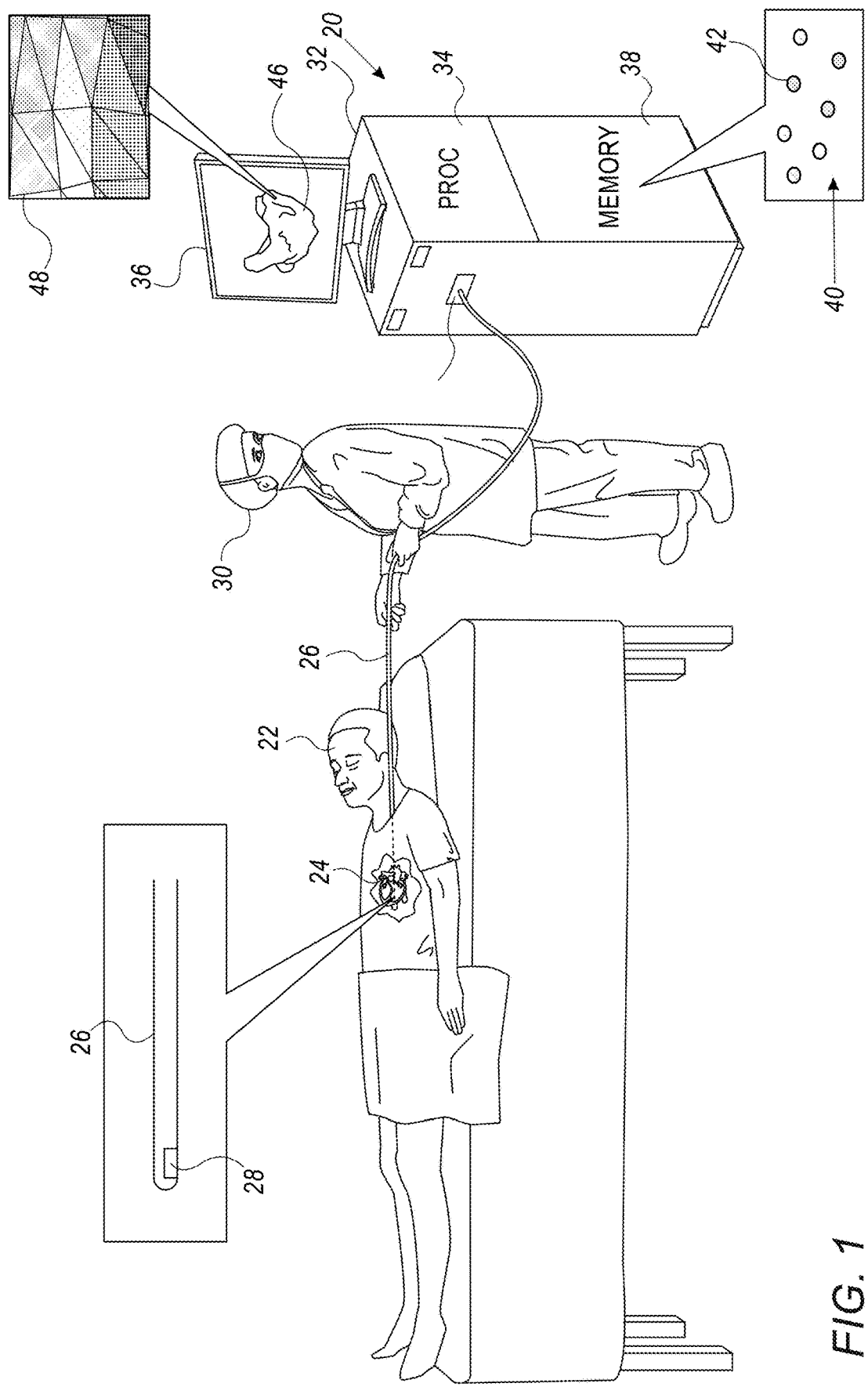
FIG. 1 is a schematic illustration of an anatomical mapping system, in accordance with some examples of the present disclosure.

Reference is initially made to FIG. 1, which is a schematic illustration of an anatomical mapping system 20, in accordance with some examples of the present disclosure.

System 20 comprises an intrabody probe 26 proximally connected to a console 32. System 20 further comprises a processor (PROC) 34 and a memory 38, which are typically contained in console 32, and a display 36, which may be disposed on console 32. Memory 38 may comprise any suitable volatile memory, such as a random access memory (RAM), and/or non-volatile memory, such as a flash memory.

Figure 3:
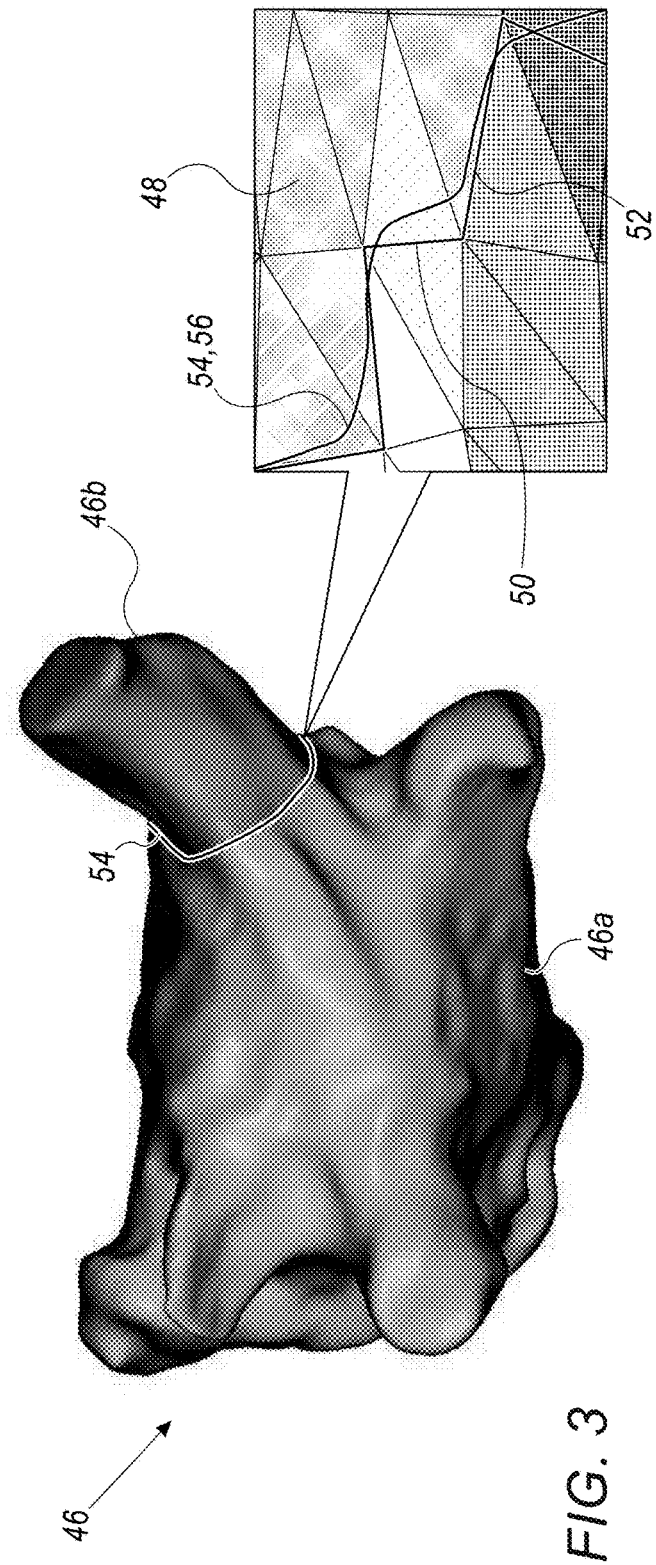
FIG. 3 is a schematic illustration of a triangle mesh, in accordance with some examples of the present disclosure.

Processor 34 is configured to compute a triangle mesh 46 including multiple triangles 48 representing a plurality of anatomical structures. As shown in FIG. 3, mesh 46 appears in the form of an anatomical model displayed to the user. The anatomical structures include a first structure and multiple second structures. In some cases, the multiple section structures are in fluid communication with the first structure but not with each other.

For example, the first structure may include at least part of a body of a chamber of the heart 24 of a subject 22, and the second structures may include appendages of the chamber and/or blood vessels connected to the chamber body. As a specific example, the first structure may include at least part of the left atrium body of heart 24, and the second structures may include the left atrial appendage and/or one or more pulmonary veins that deliver blood to the left atrium body. As another example, the first structure may include at least part of a chamber of a sinus, and the second structures may include airways connected to the chamber.

To compute mesh 46, the processor first obtains a point cloud 40, which includes multiple points 42 representing different respective locations in the body of subject 22. Points 42 are labeled as corresponding to the respective anatomical structures to which the locations, respectively, belong, and which the mesh is to represent. For example, a point 42 representing a location belonging to the left atrium body of heart 24 may be labeled as corresponding to the left atrium body.

In some examples, the processor obtains point cloud 40 without computing the point cloud; for example, the processor may receive the point cloud over a computer network or load the point cloud from an external storage drive.

In other examples, the processor computes the point cloud by sampling multiple preliminary meshes representing the anatomical structures, respectively. Subsequently to computing the point cloud, the processor may store the point cloud in memory 38, and then read the point cloud from the memory when computing mesh 46.

In such examples, the preliminary meshes are generated from a preliminary point cloud using any suitable surface-reconstruction algorithm such as the algorithm described in Lorensen, William E. and Harvey E. Cline, "Marching cubes: A high resolution 3D surface construction algorithm," ACM siggraph computer graphics 21.4 (1987): 163-169, whose disclosure is incorporated herein by reference. To generate the preliminary point cloud, a physician 30 moves the distal end of probe 26 along the surfaces of the anatomical structures as processor 34 (or a different processor) tracks the position of the distal end. Such a point cloud may be acquired by ultrasound imaging of a chamber of a heart. Alternatively, the locations of data are reported by a location sensor on the catheter, as known in the art. For example, data may be acquired using the fast anatomic mapping (FAM) functions of the CARTO® 3 System cooperatively with a mapping catheter such as the Navistar® Thermocool® catheter, both available from Biosense Webster, Inc., available from Biosense Webster, Inc., 3333 Diamond Canyon Road, Diamond Bar, Calif. 9176531A Technology Drive, Irvine, CA 92618. Processors such as are found in the CARTO® system may be programmed to carry out the functions described below by those skilled in the art.

In some such examples, to facilitate tracking the probe, one or more electromagnetic sensors 28 are coupled to the distal end of the probe, and a magnetic field is generated in the vicinity of subject 22. The magnetic field induces a location-dependent signal in sensors 28. Based on this signal, the processor ascertains the location of the distal end of the probe. Such magnetic-based tracking is disclosed, for example, in U.S. Pat. Nos. 5,391,199, 5,443,489, and 6,788,967 to Ben-Haim, U.S. Pat. No. 6,690,963 to Ben-Haim et al., U.S. Pat. No. 5,558,091 to Acker et al., and U.S. Pat. No. 6,177,792 to Govari, whose respective disclosures are incorporated herein by reference.

Alternatively or additionally, one or more electrodes coupled to the distal end of the probe may pass electric currents to a plurality of electrode patches coupled to the subject's body at different respective locations. Based on the electric currents and the body-impedance measurements derived therefrom, the processor may ascertain the location of the distal end of the probe, as taught, for example in U.S. Pat. No. 7,756,576 and in U.S. Pat. No. 7,536,218, which are hereby incorporated by reference. A hybrid technique combining such impedance-based tracking with magnetic-based tracking is described in U.S. Pat. No. 8,456,182 to Bar-Tal et al., whose disclosure is incorporated herein by reference.

Subsequently to obtaining point cloud 40, the processor applies any suitable version of the ball-pivoting algorithm (BPA) to point cloud 40, as further described below with reference to FIG. 2, thereby computing mesh 46. Subsequently to computing mesh 46, processor 34 displays the mesh on display 36.

In general, processor 34 may be embodied as a single processor, or as a cooperatively networked or clustered set of processors. In some examples, the functionality of processor 34, as described herein, is implemented solely in hardware, e.g., using one or more Application-Specific Integrated Circuits (ASICs) or Field-Programmable Gate Arrays (FPGAs). In other examples, the functionality of processor 34 is implemented at least partly in software. For example, in some examples, processor 34 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Computing the Mesh

Figure 2:
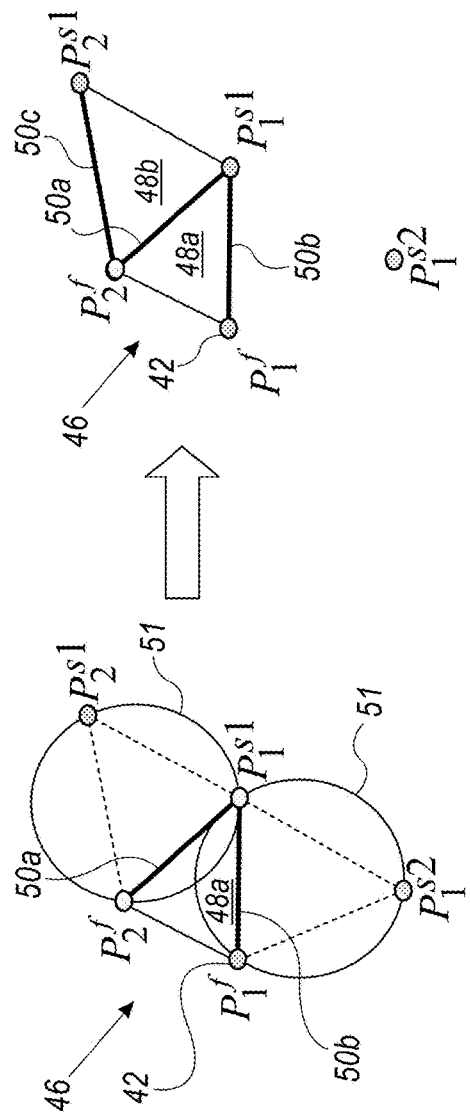
FIG. 2 is a schematic illustration of an example computation of a triangle mesh, in accordance with some examples of the present disclosure.

Reference is now made to FIG. 2, which is a schematic illustration of an example computation of mesh 46, in accordance with some examples of the present disclosure.

The processor 34 (FIG. 1) may use a mapping module to initially connect locations of the point cloud. e.g. data to define a mesh of line segments. The mesh 46 typically, although not necessarily, is a triangular mesh. In one embodiment, the processor uses the Ball-Pivoting Algorithm (BPA) to produce the mesh 46. Typically, if a BPA is used, a size of the ball is set to correspond to the size of the voxels of the subject anatomical model. Alternatively, the mesh may be generated as a Delaunay triangulation, comprising a plurality of triangles having vertices. The triangles of the triangulation may be based on Voronoi diagrams formed about the locations of the mesh. However, the processor may use any convenient method that is known in the art for forming a mesh. In this example, processor 34 (FIG. 1) is configured to apply the BPA to point cloud 40 with a constraint that none of polygons (here, triangles 48) include two points 42 labeled as corresponding to different respective ones of the second structures.

By way of example, FIG. 2 shows a scenario in which, during the application of the BPA to the point cloud, a triangle 48*a* is formed. Triangle 48*a* includes three points 42: a first point $P_1^f$, a second point $P_2^f$, and a third point $P_1^{s1}$. First point $P_1^f$ and second point $P_2^f$ are labeled as corresponding to the first structure (as indicated by the superscript "f"), which may include, for example, at least part of a chamber of a heart or at least part of a sinus. Third point $P_1^{s1}$ is labeled as corresponding to a second structure s1 (as indicated by the superscript "s1"), which may include, for example, a blood vessel or an airway.

Following the formation of triangle 48*a*, the BPA ball 51 pivots, at different respective times, around two edges of triangle 48*a*: a first edge 50*a*, which joins second point $P_2^f$ to third point $P_1^{s1}$, and a second edge 50*b*, which joins first point $P_1^f$ to third point $P_1^{s1}$. As ball 51 pivots around first edge 50*a*, the ball touches a fourth point $P_2^{s1}$, which is labeled as corresponding to second structure s1. As the ball pivots around second edge 50*b*, the ball touches a fifth point $P_1^{s2}$, which is labeled as corresponding to another second structure s2, which may include, for example, another blood vessel or airway. Thus, as indicated in FIG. 2 by the broken edges, the BPA algorithm may potentially add fourth point $P_2^{s1}$ and/or fifth point $P_1^{s2}$ to the triangle mesh.

Fourth point $P_2^{s1}$ is added, given that the resulting triangle 48*b*, which includes second point $P_2^f$, third point $P_1^{s1}$, and fourth point $P_2^{s1}$, does not violate the constraint. However, fifth point $P_1^{s2}$ is not added to the mesh, as such an addition would result in third point $P_1^{s1}$ and fifth point $P_1^{s2}$, which are labeled as corresponding to different respective second structures, belonging to the same triangle.

Segmentation

In some examples, for each of the second structures, the processor identifies multiple edges of triangles 48, each of which passes between any first one of the points labeled as corresponding to the first structure and any second one of the points labeled as corresponding to the second structure. For example, as indicated by the thickened lines in FIG. 2, for second structure s1, the processor may identify first edge 50*a*, second edge 50*b*, and a third edge 50*c*, which joins second point $P_2^f$ to fourth point $P_2^{s1}$.

Typically, these "boundary edges" are identified while applying the BPA to the cloud of points 42. For example, in response to the addition of each new point to the mesh, the processor may check whether the newly-added point is joined to a point corresponding to a different structure. If yes, the edge or edges joining the newly-added point may be identified as boundary edges. For example, in response to the addition of fourth point $P_2^{s1}$, third edge 50*c* may be identified as a boundary edge.

Reference is now made to FIG. 3, which is a schematic illustration of a mesh 46, in accordance with some examples of the present disclosure. Mesh 46 includes a first mesh portion 46*a*, which represents the surface of a left atrium body, and a second mesh portion 46*b*, which represents the surface of a pulmonary vein.

Based on the identified boundary edges, the processor displays, on the mesh, a boundary 54 between the first structure and each of the second structures. For example, in the case shown in FIG. 3, the processor displays a boundary 54 between the left atrium body and the pulmonary vein.

Typically, the identified boundary edges form a closed polyline 52. The processor may therefore display polyline 52 as the boundary. Typically, however, the processor smooths the polyline, and then displays the smoothed polyline 56 as the boundary. To smooth the polyline, the processor may use spline interpolation or any other suitable technique.

In some cases, one or more identified boundary edges diverge from polyline 52. The processor is configured to prune these diverging edges from the polyline prior to displaying or smoothing the polyline. It should also be appreciated that myriad other suitable means may be used to indicate a boundary between the structures, including, but not limited to, as a raised feature, a depression, assigning different colors to the surfaces of each of the structures, adding one or more icons at or near the boundary, and/or superimposing arrow(s) pointing to the boundary, or the like.

Example BPA Algorithm

Figure 4:
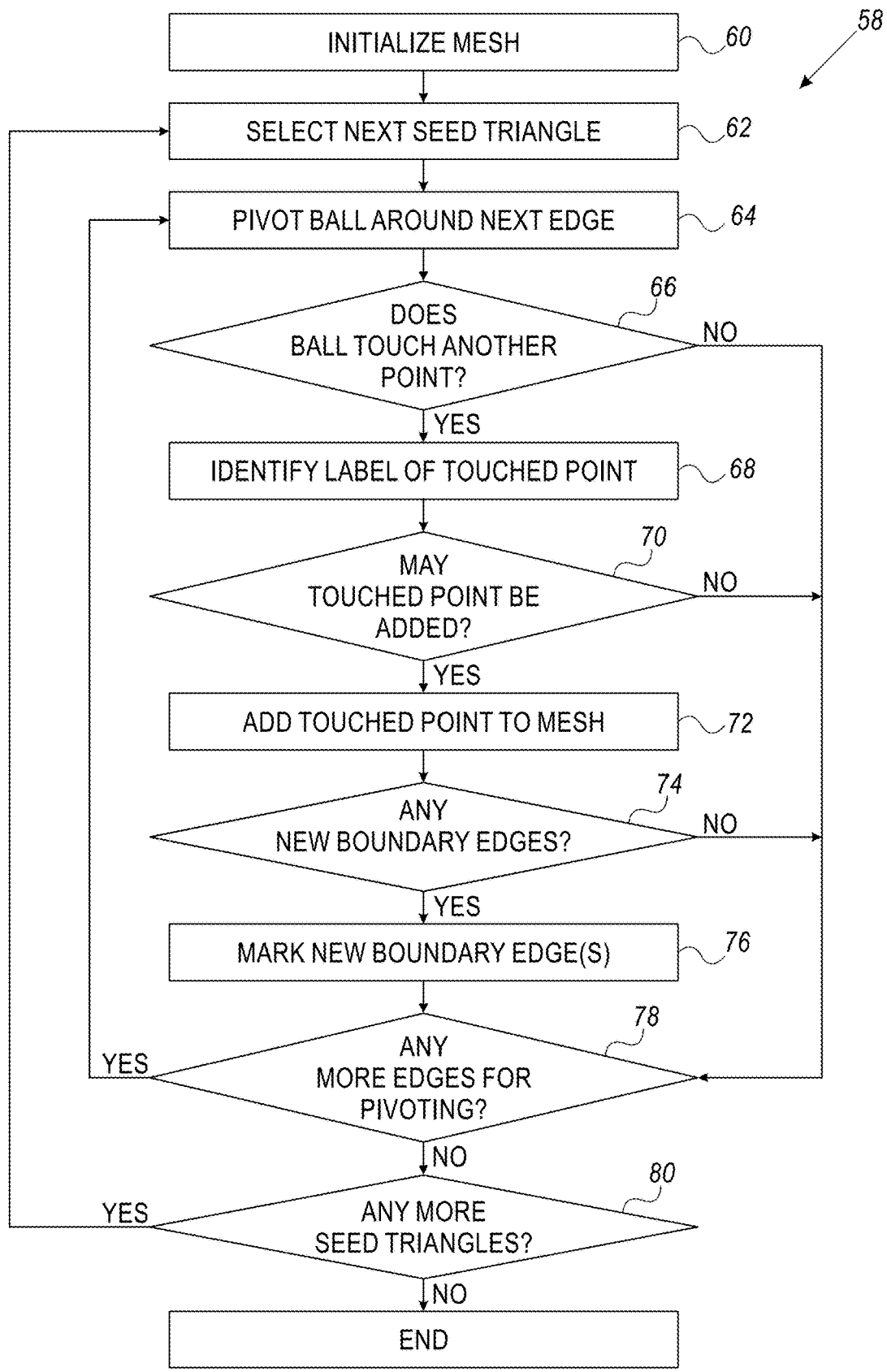
FIG. 4 is a flow diagram for an example BPA algorithm, in accordance with some examples of the present disclosure.

Reference is now made to FIG. 4, which is a flow diagram for an example BPA algorithm 58, which represents a novel improvement upon a traditional BPA algorithm, which allows accurate, automated identification of boundaries between different anatomical structures. The algorithm may be executed by processor 34 (FIG. 1) in accordance with examples of the present disclosure.

Algorithm 58 begins with an initializing step 60, at which mesh 46 (FIG. 1) is initialized with at least one triangle. As noted above, other examples within scope of the claims may operate on meshes formed of polygons other than or additional to triangles. Following initializing step 60, the processor, at a seed-selecting step 62, selects a seed triangle. Subsequently, the processor, at a pivoting step 64, pivots ball 51 (FIG. 1) around an edge of the seed triangle. The processor then checks, at a checking step 66, whether the ball touches another point. If not, the processor proceeds to another checking step 78, described below. Otherwise, the processor, at a label-identifying step 68, identifies the label of the touched point.

Subsequently to identifying the label, the processor, at another checking step 70, checks, based on the label, whether the aforementioned constraint allows the touched point to be added to the mesh. In particular, the processor checks whether either one of the edge endpoints corresponds to one of the second structures, and if so, whether the touched point corresponds to the same second structure. If the touched point does not correspond to any of the second structures, or if the touched point corresponds to the same second structure as one or both of the endpoints, the processor concludes that the touched point may be added.

If the touched point is constrained from being added to the mesh, the processor proceeds to checking step 78. Otherwise, the processor, at a point-adding step 72, adds the touched point to the mesh. Subsequently, the processor checks, at another checking step 74, whether one or both of the edges that join the new point to the mesh is a boundary edge. If yes, the processor marks the boundary edge(s) at a marking step 76. Subsequently, or if no boundary edges are marked, the processor performs checking step 78.

At checking step 78, the processor checks whether any edges for pivoting remain. If yes, the processor returns to pivoting step 64, at which the processor pivots the BPA ball around the next edge. Otherwise, the processor checks, at another checking step 80, whether any more seed triangles remain. If yes, the processor returns to seed-selecting step 62, at which the processor selects the next seed triangle. Otherwise, algorithm 58 ends.

Subsequently to executing algorithm 58, the processor displays the mesh. As described above with reference to FIG. 3, the processor may overlay, on the mesh, one or more boundaries 54, which may be defined based on the marked boundary edges. For example, each boundary may be a closed curve that smoothly interpolates a closed polyline defined by the marked boundary edges.

EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

1. A system (20) includes a display (36) and a processor (34). The processor is configured to obtain a point cloud (40) including multiple points (42) representing different respective locations in a body of a subject (22), the points being labeled as corresponding to respective anatomical structures to which the locations, respectively, belong. The anatomical structures include a first structure and multiple second structures. The processor is further configured to form a mesh (46) including multiple triangles (48) representing the anatomical structures, by applying a ball-pivoting algorithm to the point cloud with a constraint that none of the triangles include two of the points labeled as corresponding to different respective ones of the second structures. The processor is further configured to display the mesh on the display.

2. The system (20) according to Example 1, wherein the first structure includes at least part of a chamber of a heart (24).

3. The system (20) according to Example 1, wherein the first structure includes at least part of a sinus.

4. The system (20) according to any one of Examples 1-3, wherein the processor (34) is further configured to:
  for each of the second structures:
    identify multiple edges of the triangles (48), each of which passes between any first one of the points (42) labeled as corresponding to the first structure and any second one of the points labeled as corresponding to the second structure, and
    based on the identified edges, display, on the mesh (46), a boundary (54) between the first structure and the second structure.

5. The system (20) according to claim 4, wherein the identified edges form a closed polyline (52), and wherein the processor (34) is configured to display the boundary (54) by:
  smoothing the polyline, and
  displaying the smoothed polyline (56).

6. The system (20) according to any one of Examples 4-5, wherein the processor (34) is configured to identify the edges for each of the second structures while applying the ball-pivoting algorithm to the point cloud (40).

7. The system (20) according to any one of Examples 1-6, wherein the processor (34) is configured to compute the point cloud (40) by sampling multiple preliminary meshes representing the anatomical structures, respectively.

8. A method includes obtaining a point cloud (40) including multiple points (42) representing different respective locations in a body of a subject (22), the points being labeled as corresponding to respective anatomical structures to which the locations, respectively, belong. The anatomical structures including a first structure and multiple second structures The method further includes computing a mesh (46) including multiple triangles (48) representing the anatomical structures, by applying a ball-pivoting algorithm to the point cloud with a constraint that none of the triangles include two of the points labeled as corresponding to different respective ones of the second structures. The method further includes displaying the mesh.

9. The method according to Example 8, wherein the first structure includes at least part of a chamber of a heart (24).

10. The method according to Example 8, wherein the first structure includes at least part of a sinus.

11. The method according to any one of Examples 8-10, further comprising:
  for each of the second structures:
    identifying multiple edges of the triangles (48), each of which passes between any first one of the points (42) labeled as corresponding to the first structure and any second one of the points labeled as corresponding to the second structure, and
    based on the identified edges, displaying, on the mesh (46), a boundary (54) between the first structure and the second structure.

12. The method according to Example 11, wherein the identified edges form a closed polyline (52), and wherein displaying the boundary (54) comprises:
  smoothing the polyline; and
  displaying the smoothed polyline (56).

13. The method according to any one of Examples 11-12, wherein identifying the edges for each of the second structures comprises identifying the edges while applying the ball-pivoting algorithm to the point cloud (40).

14. The method according to any one of Examples 8-13, wherein obtaining the point cloud (40) comprises computing the point cloud by sampling multiple preliminary meshes representing the anatomical structures, respectively.

15. A computer software product comprises a tangible non-transitory computer-readable medium in which program instructions are stored. The instructions, when read by a processor (34), cause the processor to obtain a point cloud (40) including multiple points (42) representing different respective locations in a body of a subject (22), the points being labeled as corresponding to respective anatomical structures to which the locations, respectively, belong. The anatomical structures include a first structure and multiple second structures. The instructions further cause the processor to compute a mesh (46) including multiple triangles (48) representing the anatomical structures, by applying a ball-pivoting algorithm to the point cloud with a constraint that none of the triangles include two of the points labeled as corresponding to different respective ones of the second structures. The instructions further cause the processor to display the mesh or a smoothed model created therefrom.

It will be appreciated by persons skilled in the art that the present disclosure is not limited to what has been particularly shown and described hereinabove. Rather, the scope of the present disclosure includes both combinations and sub-combinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   a display; and
   a processor, configured to:
   obtain a point cloud including multiple points representing different respective locations in a body of a subject, the points being labeled as corresponding to respective anatomical structures to which the locations, respectively, belong,
   the anatomical structures including a first structure and multiple second structures, and
   compute a mesh including multiple triangles representing the anatomical structures, by applying a ball-pivoting algorithm to the point cloud with a constraint that none of the triangles include two of the points labeled as corresponding to different respective ones of the second structures.

2. The system according to claim 1, wherein the first structure includes at least part of a chamber of a heart.

3. The system according to claim 1, wherein the first structure includes at least part of a sinus.

4. The system according to claim 1, wherein the processor is further configured to:
   for each of the second structures:
   identify multiple edges of the triangles, each of which passes between any first one of the points labeled as corresponding to the first structure and any second one of the points labeled as corresponding to the second structure, and
   based on the identified edges, display, on the mesh, a boundary between the first structure and the second structure.

5. The system according to claim 4, wherein the identified edges form a closed polyline, and wherein the processor is configured to display the boundary by:
   smoothing the polyline, and
   displaying the smoothed polyline.

6. The system according to claim 4, wherein the processor is configured to identify the edges for each of the second structures while applying the ball-pivoting algorithm to the point cloud.

7. The system according to claim 1, wherein the processor is configured to compute the point cloud by sampling multiple preliminary meshes representing the anatomical structures, respectively.

8. A method, comprising:
   obtaining a point cloud including multiple points representing different respective locations in a body of a subject, the points being labeled as corresponding to respective anatomical structures to which the locations, respectively, belong,
   the anatomical structures including a first structure and multiple second structures; and
   computing a mesh including multiple triangles representing the anatomical structures, by applying a ball-pivoting algorithm to the point cloud with a constraint that none of the triangles include two of the points labeled as corresponding to different respective ones of the second structures.

9. The method according to claim 8, wherein the first structure includes at least part of a chamber of a heart.

10. The method according to claim 8, wherein the first structure includes at least part of a sinus.

11. The method according to claim 8, further comprising:
    for each of the second structures:
    identifying multiple edges of the triangles, each of which passes between any first one of the points labeled as corresponding to the first structure and any second one of the points labeled as corresponding to the second structure, and
    based on the identified edges, displaying, on the mesh, a boundary between the first structure and the second structure.

12. The method according to claim 11, wherein the identified edges form a closed polyline, and wherein displaying the boundary comprises:
    smoothing the polyline; and
    displaying the smoothed polyline.

13. The method according to claim 11, wherein identifying the edges for each of the second structures comprises identifying the edges while applying the ball-pivoting algorithm to the point cloud.

14. The method according to claim 8, wherein obtaining the point cloud comprises computing the point cloud by sampling multiple preliminary meshes representing the anatomical structures, respectively.

15. A computer software product comprising a tangible non-transitory computer-readable medium in which program instructions are stored, which instructions, when read by a processor, cause the processor to:
    obtain a point cloud including multiple points representing different respective locations in a body of a subject, the points being labeled as corresponding to respective anatomical structures to which the locations, respectively, belong,
    the anatomical structures including a first structure and multiple second structures in fluid communication with the first structure but not with each other, and
    compute a mesh including multiple triangles representing the anatomical structures, by applying a ball-pivoting algorithm to the point cloud with a constraint that none of the triangles include two of the points labeled as corresponding to different respective ones of the second structures.

16. The computer software product according to claim 15, wherein the first structure includes at least part of a chamber of a heart.

17. The computer software product according to claim 15, wherein the first structure includes at least part of a sinus.

18. The computer software product according to claim 15, wherein the instructions further cause the processor to:
    for each of the second structures:
    identify multiple edges of the triangles, each of which passes between any first one of the points labeled as corresponding to the first structure and
    any second one of the points labeled as corresponding to the second structure, and
    based on the identified edges, display, on the mesh, a boundary between the first structure and the second structure.

19. The computer software product according to claim 18, wherein the identified edges form a closed polyline, and
    wherein the instructions cause the processor to display the boundary by:
    smoothing the polyline, and
    displaying the smoothed polyline.

20. The computer software product according to claim 18, wherein the instructions cause the processor to identify the edges for each of the second structures while applying the ball-pivoting algorithm to the point cloud.

* * * * *